(12) United States Patent
Jiaang et al.

(10) Patent No.: US 7,687,504 B2
(45) Date of Patent: Mar. 30, 2010

(54) PYRROLIDINE COMPOUNDS

(75) Inventors: Weir-Torn Jiaang, Taichung (TW); Xin Chen, Taipei County (TW); Su-Ying Wu, Tainan (TW); Yu-Sheng Chao, Taipei (TW); Hsing-Pang Hsieh, Taipei (TW)

(73) Assignee: National Health Research Institutes, Miaoli County (TW)

( * ) Notice: Subject to any disclaimer, the term of this patent is extended or adjusted under 35 U.S.C. 154(b) by 1282 days.

(21) Appl. No.: 11/077,551

(22) Filed: Mar. 9, 2005

(65) Prior Publication Data
US 2005/0222222 A1 Oct. 6, 2005

Related U.S. Application Data

(60) Provisional application No. 60/551,419, filed on Mar. 9, 2004, provisional application No. 60/617,684, filed on Oct. 12, 2004.

(51) Int. Cl.
*A61K 31/497* (2006.01)
*A61K 31/47* (2006.01)
*A61K 31/44* (2006.01)
*A61K 31/425* (2006.01)
*A61K 31/40* (2006.01)
*C07D 401/12* (2006.01)
*C07D 403/12* (2006.01)
*C07D 217/00* (2006.01)
*C07D 277/62* (2006.01)
*C07D 207/09* (2006.01)

(52) U.S. Cl. ........... 514/252.13; 514/307; 514/340; 514/367; 514/414; 514/428; 544/360; 544/372; 546/146; 546/279.1; 548/152; 548/465; 548/530

(58) Field of Classification Search ........ 548/453, 548/152, 465, 530; 514/422, 252.13, 307, 514/340, 367, 414, 428; 544/360, 372; 546/146, 546/279.1

See application file for complete search history.

(56) References Cited

U.S. PATENT DOCUMENTS 5,852,007 A 12/1998 Chatterjee

2007/0093492 A1 4/2007 Jiaang et al.

FOREIGN PATENT DOCUMENTS

| EP | 1 333 025 | | 8/2003 |
| EP | 1333025 | * | 8/2003 |
| EP | 1 595 833 | | 11/2005 |
| WO | WO 03/037327 | | 5/2003 |
| WO | WO2004/043940 | | 5/2004 |
| WO | WO 2004/067509 | | 8/2004 |
| WO | WO2004/067509 | | 8/2004 |
| WO | WO 2004/067509 A1 | * | 8/2004 |
| WO | WO2004/089362 | | 10/2004 |
| WO | WO2004/103993 | | 12/2004 |
| WO | WO 2004/103993 A1 | * | 12/2004 |

OTHER PUBLICATIONS

Edmondson et al., "Discovery of Pitent and Selective Orally Bioavailable Beta-Substituted Phenylalanine Derived Dipeptidyl Peptidase IV Inhibitors," Bioorganic & Medicinal Chemistry Letters, 15(12):3048-3052.
Hughes et al., NVP-DPP728 (1-[[[2-[(5-Cyanopyridin-2-yl)amino]ethyl]amino]acetyl]-2-cyano-(S)-pyrrolidine), a Slow-Binding Inhibitor of Dipeptidyl Peptidase IV, Biochemistry 38:11597-11603, 1999.
Villhauer et al., 1-[2-[(5-Cyanopyridin-2-yl)amino]-ethylamino]acetyl-2-(S)-pyrrolidine-carbonitrile: A Potent, Selective, and Orally Bioavailable Dipeptidyl Peptidase IV Inhibitor with Antihyperglycemic Properties, J. Med. Chem. 45:2362-2365, 2002.
Villhauer et al., 1-[[(3-Hydroxy-1-adamantyl)amino]acetyl]-2-cyano-(s)-pyrrolidine: A Potent, Selective, and Orally Bioavailable Dipeptidyl Peptidase IV Inhibitor with Antihyperglycemic Properties, J. Med. Chem. 46:2774-2789, 2003.

* cited by examiner

*Primary Examiner*—Joseph R Kosack
(74) *Attorney, Agent, or Firm*—Occhiuti Rohlicek & Tsao LLP

(57) ABSTRACT

A compound of the following formula:

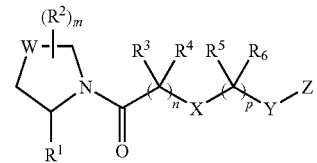

wherein $R^1$, $R^2$, $R^3$, $R^4$, $R^5$, $R^6$, W, X, Y, Z, m, n, and p are as defined herein. This invention also covers methods for inhibiting dipeptidyl peptidase IV or VIII, or treating Type II diabetes with such a compound.

21 Claims, No Drawings

PYRROLIDINE COMPOUNDS

CROSS REFERENCE TO RELATED APPLICATIONS

Pursuant to 35 USC §119(e), this application claims priority to U.S. Provisional Application Ser. No. 60/551,419, filed Mar. 9, 2004, and U.S. Provisional Application Ser. No. 60/617,684, filed Oct. 12, 2004, the contents of which are incorporated herein by reference.

BACKGROUND

Glucagon-like peptide-1 (GLP-1) is a gut hormone produced by intestinal endocrine L-cells in response to nutrient ingestion. GLP-1 inhibits glucagon secretion and stimulates glucose-dependent insulin release from the pancreas. It was observed that administration of GLP-1 significantly lowered blood glucose levels in Type II diabetes patients (Zander M, et al. *Lancet* 2002, 359: 824-830).

However, GLP-1, whether endogenously or exogenously administered, degrades rapidly. (Kieffer T. J., et al. *Endocrinology* 1995, 136: 3585-3596; and Mentlein R, et al. *Eur. J. Biochem.* 1993, 214: 829-839). The degradation is attributable to dipeptidyl peptidase IV (DPP-IV), a member of the prolyl peptidase family. Recent clinical data indicate that inhibiting DPP-IV resulted in enhanced insulin secretion, reduced plasma glucose concentrations, and improved pancreatic β-cell function (Pederson R. A., et al. *Diabetes* 1998, 47: 1253-1258; and Ahren B, et al. *Diabetes Care* 2002, 25: 869-875). Thus, inhibitors of DPP-IV are potential drug candidates for Type II diabetes.

Dipeptidyl peptidase VIII (DPP-VIII), another member of the prolyl peptidase family, is highly homologuous to DPP-IV. Some functions ascribed to DPP-IV have been found to derive from the activity of DPP-VIII (Rosenblum J. S., et al. *Current Opinion in Chemical Biology* 2003, 7: 496-504).

SUMMARY

This invention is based on a surprising discovery that a group of pyrrolidine compounds inhibit DPP-IV and DPP-VIII.

One aspect of this invention relates to pyrrolidine compounds of the following general formula:

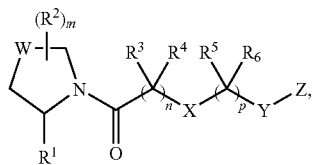

wherein $R^1$ is H or CN; each of $R^2$, $R^3$, $R^4$, $R^5$, and $R^6$, independently, is H, halo, nitro, cyano, amino, hydroxy, alkyl, haloalkyl, alkoxy, aryloxy, aralkyl, cyclyl, heterocyclyl, aryl, or heteroaryl; m is 0, 1, 2, 3, 4, or 5; each of n and p, independently, is 0, 1, 2, 3, or 4; W is $CR^aR^{a'}$, $NR^a$, O, or S, $R^a$ and $R^{a'}$, independently, being H, halogen, alkyl, or aryl; X is O, S, or $CR^b(NR^{b'}R^{b''})$, $R^b$, $R^{b'}$, and $R^{b''}$, independently, being H, alkyl, or aryl; Y is

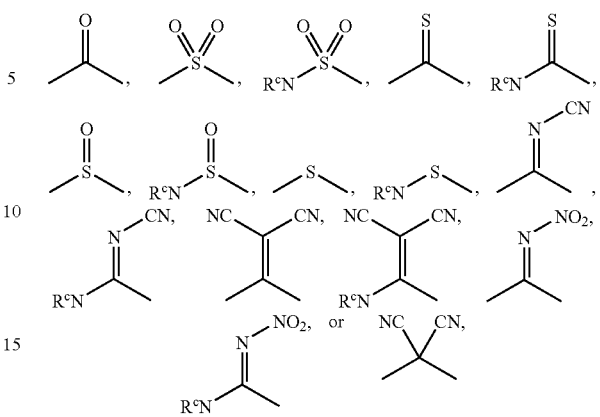

in which $R^c$ is H, alkyl, or aryl; and Z is $NR^7R^8$, in which each of $R^7$ and $R^8$, independently, is H, alkyl, alkoxyalkyl, haloalkyl, cyclyl, heterocyclyl, aryl, aralkyl, heteroaryl, or heteroaralkyl; or $NR^7R^8$, together, is a 3-8 membered ring having 1 or 2 heteroatoms, optionally substituted with halo, CN, $NO_2$, $-OR^d$, alkyl, aryl, heteroaryl, haloalkyl, $-OR^d$, $-C(O)R^d$, $-SR^d$, $-S(O)R^d$, $-S(O)_2R^d$, $-NR^dR^{d'}$, $-C(O)OR^d$, $-C(O)NR^dR^{d'}$, $-OC(O)R^d$, $-NR^dC(O)R^{d'}$, $-NR^dC(O)OR^{d'}$, or $-NR^dC(O)NR^{d'}R^{d''}$, or optionally fused with one of cyclyl, heterocyclyl, aryl, and heteroaryl, each of $R^d$, $R^{d'}$, and $R^{d''}$, independently, being H, alkyl, or aryl.

In some of the just-described pyrrolidine compounds, $R^1$ is CN, W is $CH_2$, Y is

m is 0, n is 0, p is 1, each of $R^5$ and $R^6$ is H, X is $CH(NH_2)$, or Z is $NR^7R^8$, $R^7$ being H and $R^8$ being alkyl, aryl, or aralkyl; or a 5 or 6-membered ring or

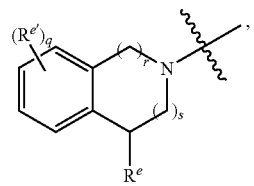

in which $R^e$ is alkyl, haloalkyl, alkoxy, aryloxy, aralkyl, cyclyl, heterocyclyl, aryl, or heteroaryl, $R^{e'}$ being halo, nitro, cyano, amino, hydroxy, alkyl, haloalkyl, alkoxy, aryloxy, aralkyl, cyclyl, heterocyclyl, aryl, or heteroaryl, q is 0, 1, 2, 3, or 4, and each of r and s, independently, is 0, 1, or 2.

Another aspect of this invention relates to pyrrolidine compounds of the above general formula, wherein $R^1$ is H or CN; each of $R^2$, $R^3$, $R^4$, $R^5$, and $R^6$, independently, is H, halo, nitro, cyano, amino, hydroxy, alkyl, haloalkyl, alkoxy, aryloxy, aralkyl, cyclyl, heterocyclyl, aryl, or heteroaryl; m is 0, 1, 2, 3, 4, or 5; each of n and p, independently, is 0, 1, 2, 3, or 4; W is $CR^aR^{a'}$, $NR^a$, O, or S, in which $R^a$ and $R^{a'}$, independently, is H, halogen, alkyl, or aryl; X is $NR^b$, in which $R^b$ is H, alkyl, or aryl; Y is

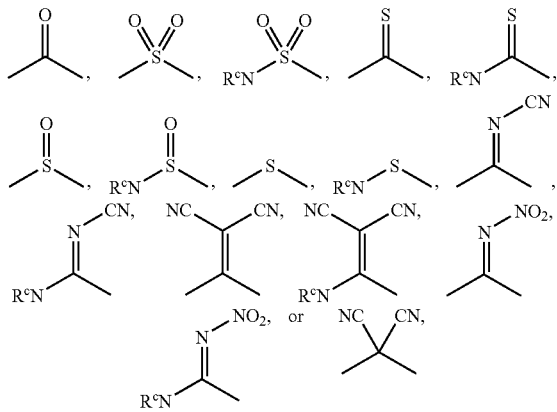

in which $R^c$ is H, alkyl, or aryl; and Z is $NR^7R^8$, in which each of $R^7$ and $R^8$, independently, is H; alkyl; alkoxyalkyl; haloalkyl; aralkyl; heteroaralkyl; a 3-8 membered monocyclic ring optionally substituted with halo, CN, $NO_2$, $-OR^d$, alkyl, aryl, heteroaryl, haloalkyl, $-OR^d$, $-C(O)R^d$, $-SR^d$, $-S(O)R^d$, $-S(O)_2R^d$, $-NR^dR^{d'}$, $-C(O)OR^d$, $-C(O)NR^dR^{d'}$, $-OC(O)R^d$, $-NR^dC(O)R^d$, $-NR^dC(O)OR^{d'}$, or $-R^dC(O)NR^{d'}R^{d''}$; or

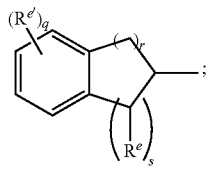

or $NR^7R^8$, together, is

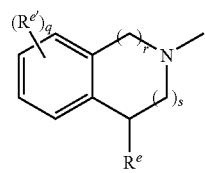

or a 3-8 membered monocyclic ring having 1 or 2 heteroatoms, optionally substituted with halo, CN, $NO_2$, $-OR^d$, alkyl, aryl, heteroaryl, haloalkyl, $-OR^d$, $-C(O)R^d$, $-SR^d$, $-S(O)R^d$, $-S(O)_2R^d$, $-NR^dR^{d'}$,
$-C(O)OR^d$, $-C(O)NR^dR^{d'}$, $-OC(O)R^d$, $-NR^dC(O)R^d$, $-NR^dC(O)OR^d$, or $-NR^dC(O)NR^{d'}R^{d''}$; each of $R^d$, $R^{d'}$, and $R^{d''}$, independently, being H, alkyl, or aryl; each of $R^e$ and $R^{e'}$, independently, being halo, nitro, cyano, amino, hydroxy, alkyl, haloalkyl, alkoxy, aryloxy, aralkyl, cyclyl, heterocyclyl, aryl, or heteroaryl; q being 0, 1, 2, 3, or 4; and each of r and s, independently, being 0, 1, or 2.

In some of the just-described pyrrolidine compounds, W is $CH_2$, $R^1$ is CN, m is 0, Y is

X is NH, n is 1, p is 2, or Z is $NR^7R^8$, in which $R^7$ is H or alkyl and $R^8$ is aralkyl, or $R^7$ is H and $R^8$ is

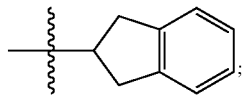

or $NR^7R^8$, together, is a 5- or 6-membered monocylic ring or

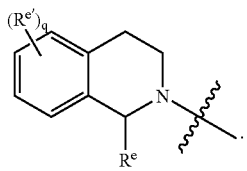

Still another aspect of this invention relates to pyrrolidine compounds of the above general formula, wherein $R^1$ is H or CN; each of $R^2$, $R^3$, $R^4$, $R^5$, and $R^6$, independently, is H, halo, nitro, cyano, amino, hydroxy, alkyl, haloalkyl, alkoxy, aryloxy, aralkyl, cyclyl, heterocyclyl, aryl, or heteroaryl; m is 0, 1, 2, 3, 4, or 5; each of n and p, independently, is 0, 1, 2, 3, or 4; W is $CR^aR^{a'}$, $NR^a$, O, or S, in which $R^a$ and $R^{a'}$, independently, is H, halogen, alkyl, or aryl; X is $NR^b$, O, S, or $CR^b(NR^{b'}R^{b''})$, in which $R^b$, $R^{b'}$, and $R^{b''}$, independently, is H, alkyl, or aryl; Y is

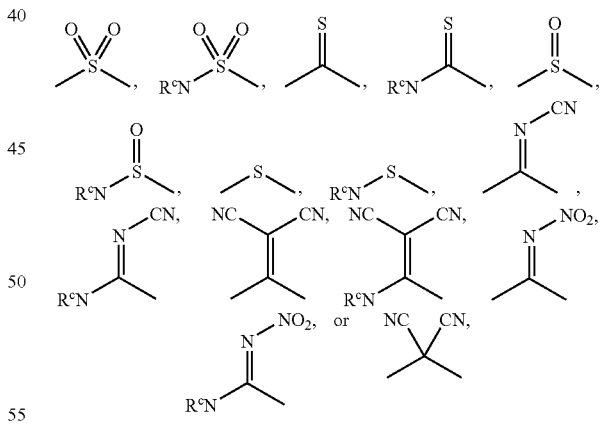

in which $R^c$ is H, alkyl, or aryl; and Z is H, amino, alkyl, cyclyl, heterocyclyl, aryl, aralkyl, or heteroaryl.

In some of the just-described pyrrolidine compounds, W is $CH_2$, $R^1$ is CN, m is 0, X is $CHNH_2$ or NH, Y is

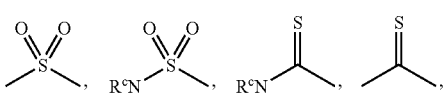

-continued
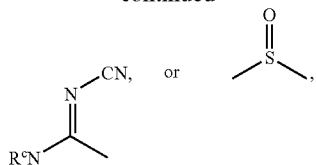
Z is cyclyl (e.g.,
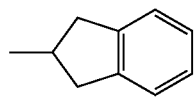
) or heterocyclyl (e.g.,
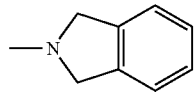
).
Shown below are exemplary compounds of this invention:
Compound 1
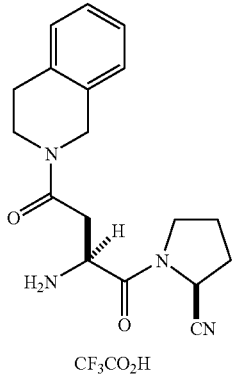
CF$_3$CO$_2$H
Compound 2
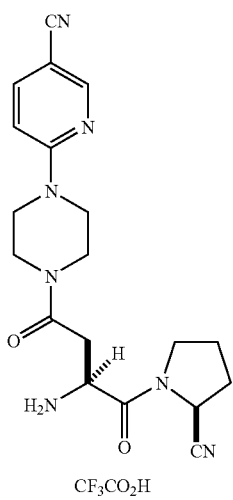
CF$_3$CO$_2$H
Compound 3
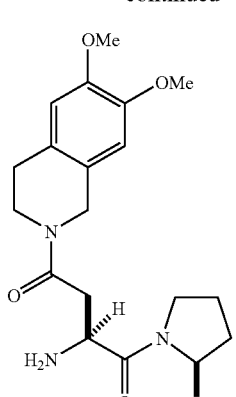
CF$_3$CO$_2$H
Compound 4
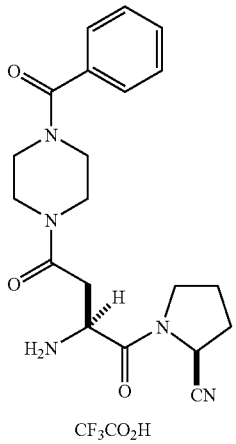
CF$_3$CO$_2$H
Compound 5
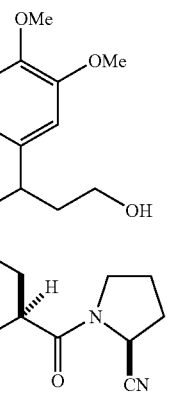
CF$_3$CO$_2$H -continued Compound 6

Compound 7

Compound 8

Compound 9

Compound 10

Compound 11

Compound 12

Compound 13, Compound 14, Compound 15, Compound 16, Compound 17, Compound 18, Compound 19, Compound 20

Compound 21
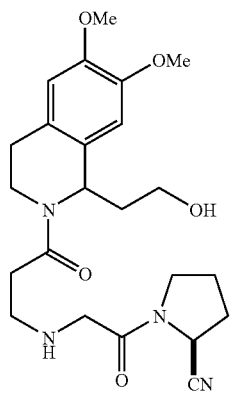
Compound 22
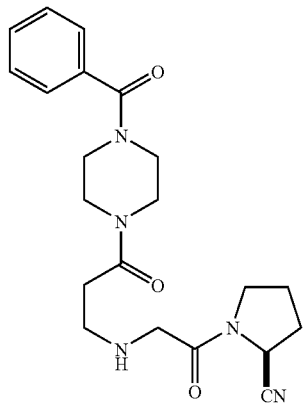
Compound 23
Compound 24
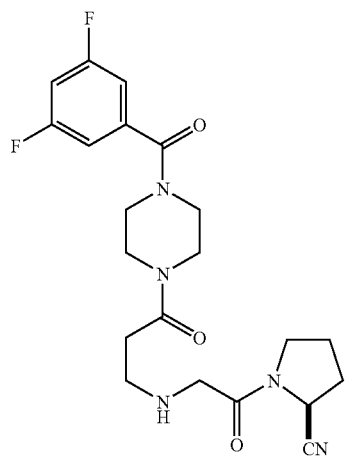
Compound 25
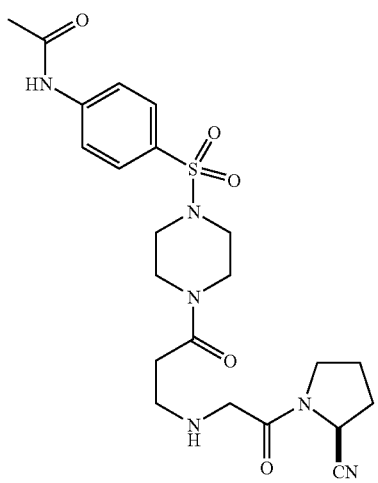
Compound 26
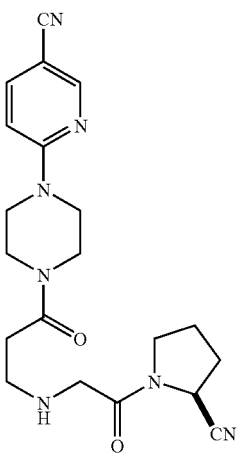

-continued
Compound 27
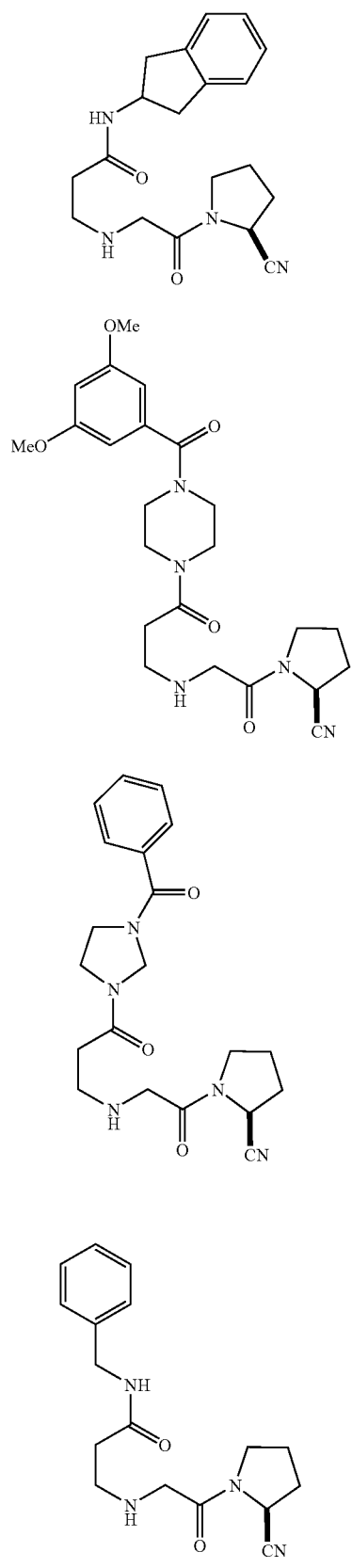
Compound 28
Compound 29
Compound 30
-continued
Compound 31
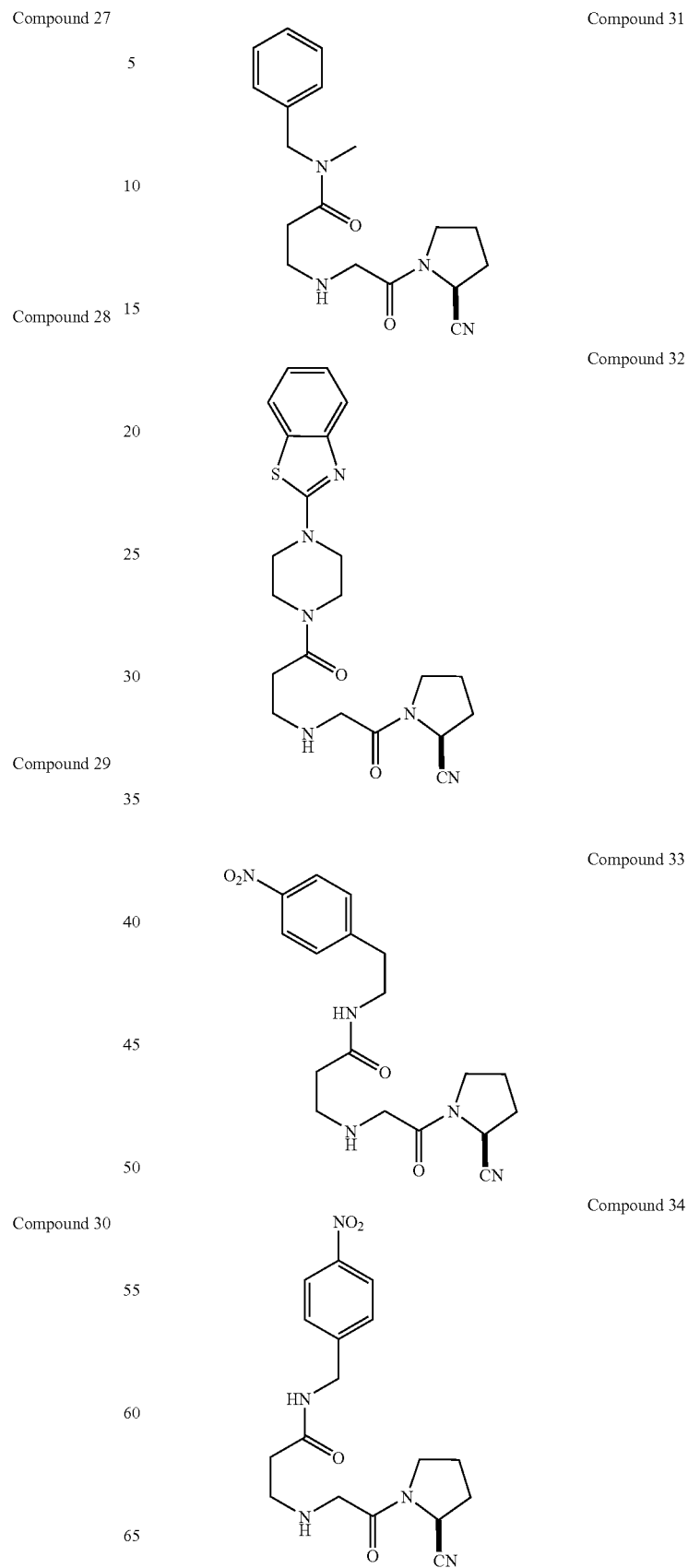
Compound 32
Compound 33
Compound 34

-continued

Compound 35

Compound 36

Compound 37

Compound 38

Compound 39

Compound 40

Compound 41

Compound 42

-continued

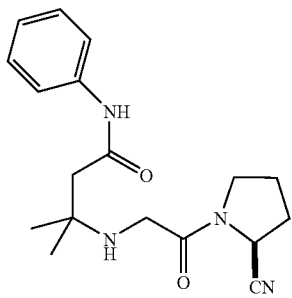

Compound 43

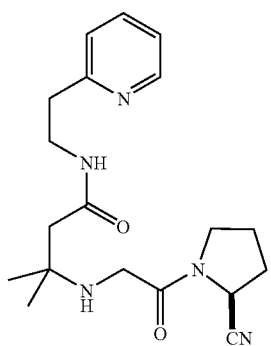

Compound 44

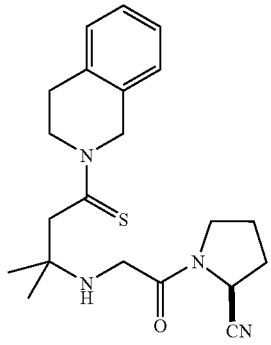

Compound 45

The term "alkyl" herein refers to a straight or branched hydrocarbon, containing 1-10 carbon atoms. Examples of alkyl groups include, but are not limited to, methyl, ethyl, n-propyl, i-propyl, n-butyl, i-butyl, and t-butyl. The term "alkoxy" refers to an —O-alkyl. The term "alkoxyalkyl" refers to an alkyl group substituted with one or more alkoxy groups. The term "haloalkyl" refers to an alkyl group substituted with one or more halo groups. The term "hydroxyalkyl" refers to an alkyl group substituted with one or more hydroxy groups.

The term "aryl" refers to a 6-carbon monocyclic, 10-carbon bicyclic, 14-carbon tricyclic aromatic ring system wherein each ring may have 1 to 4 substituents. Examples of aryl groups include, but are not limited to, phenyl, naphthyl, and anthracenyl. The term "aryloxy" refers to an —O-aryl. The term "aralkyl" refers to an alkyl group substituted with an aryl group.

The term "cyclyl" refers to a saturated and partially unsaturated cyclic hydrocarbon group having 3 to 12 carbons. Examples of cyclyl groups include, but are not limited to, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having one or more heteroatoms (such as O, N, or S). Examples of heteroaryl groups include pyridyl, furyl, imidazolyl, benzimidazolyl, pyrimidinyl, thienyl, quinolinyl, indolyl, and thiazolyl. The term "heteroaralkyl" refers to an alkyl group substituted with a heteroaryl group.

The term "heterocyclyl" refers to a nonaromatic 5-8 membered monocyclic, 8-12 membered bicyclic, or 11-14 membered tricyclic ring system having one or more heteroatoms (such as O, N, or S). Examples of heterocyclyl groups include, but are not limited to, piperazinyl, pyrrolidinyl, dioxanyl, morpholinyl, and tetrahydrofuranyl.

Alkyl, cyclyl, heterocyclyl, aryl, heteroaryl, aralkyl, heteroaralkyl, alkoxy, and aryloxy mentioned herein include both substituted and unsubstituted moieties. Examples of substituents include, but are not limited to, halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cyclyl, heterocyclyl, in which alkyl, alkenyl, alkynyl, alkyloxy, aryl, heteroaryl cyclyl, and heterocyclyl may further substituted.

The monocyclic ring mentioned herein is either substituted or unsubstituted, but cannot be fused with another aromatic or non-aromatic ring.

The pyrrolidine compounds described above include their pharmaceutically acceptable salts and prodrugs, if applicable. Such a salt can be formed between a positively charged ionic group in an pyrrolidine compound (e.g., ammonium) and a negatively charged counterion (e.g., trifluoroacetate). Likewise, a negatively charged ionic group in a pyrrolidine compound (e.g., carboxylate) can also form a salt with a positively charged counterion (e.g., sodium, potassium, calcium, or magnesium). The pyrrolidine compounds may contain a nonaromatic double bond and one or more asymmetric centers. Thus, they can occur as racemic mixtures, single enantiomers, individual diastereomers, diastereomeric mixtures, and cis- or trans-isomeric forms. All such isomeric forms are contemplated.

The pyrrolidine compounds described above can be used to inhibit DPP-IV or DPP-VIII. Accordingly, another aspect of this invention relates to a method of inhibiting DPP-IV or DPP-VIII with one or more of the pyrrolidine compounds. As inhibition of DPP-IV results in reduced blood glucose levels and enhanced insulin secretion, the compounds of this invention can be also used to treat Type II diabetes. Thus, this invention further covers a method of treating Type II diabetes by administering to a subject in need thereof an effective amount of one or more of the pyrrolidine compounds.

Also within the scope of this invention is a pharmaceutical composition containing one or more of the above-described pyrrolidine compounds and a pharmaceutically acceptable carrier, as well as use of the composition for the manufacture of a medicament for treating Type II diabetes.

The details of many embodiments of the invention are set forth in the description below. Other features, objects, and advantages of the invention will be apparent from the description and the claims.

DETAILED DESCRIPTION

The pyrrolidine compounds of this invention can be synthesized by methods well known in the art. Six exemplary synthetic routes are shown in Schemes 1-6 below.

Scheme 1

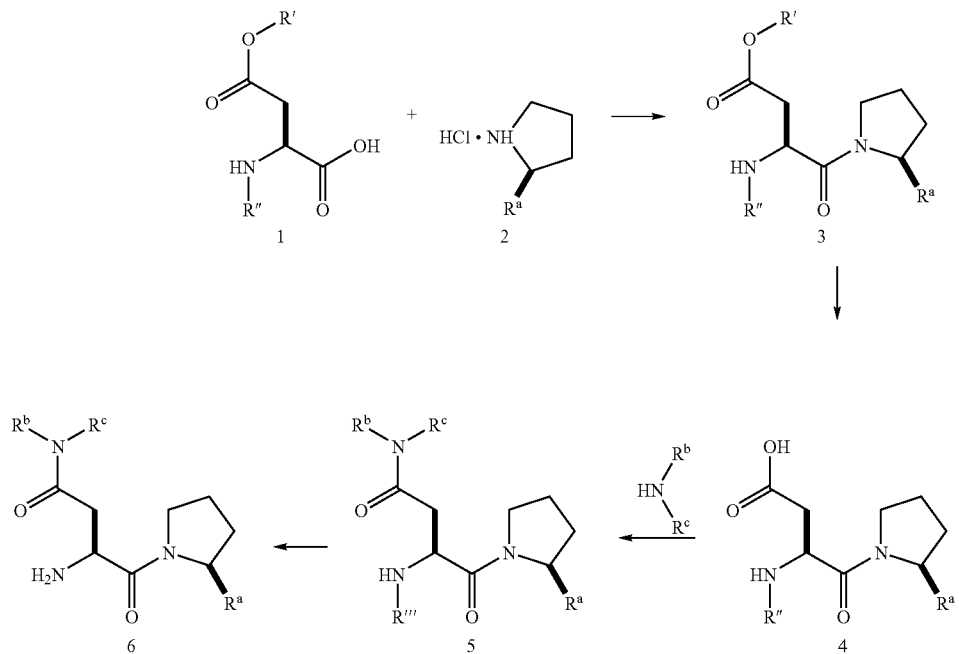

In Scheme 1, the starting compound is amino-substituted dicarboxylic acid (1) in which an amino group and one of two carboxy groups are protected. This compound is reacted with 2-substituted pyrrolidine hydorchloride salt (2) to give monoamide intermediate (3). Note that synthesis of 2-substituted pyrrolidine hydrochloride salt (2) is well known in the art. For example, pyrrolidine-2-carbonitrile hydrochloride salt can be prepared by the procedure described in *Bioorg. Med. Chem. Lett.* 1996, 6: 1163. Removing the carboxy protected group of the intermediate (3) affords monoamide monoacid compound (4), which subsequently is coupled with amine to provide diamide compound (5). Deprotection of compound (5) provides desired pyrrolidine compound (6).

Scheme 2

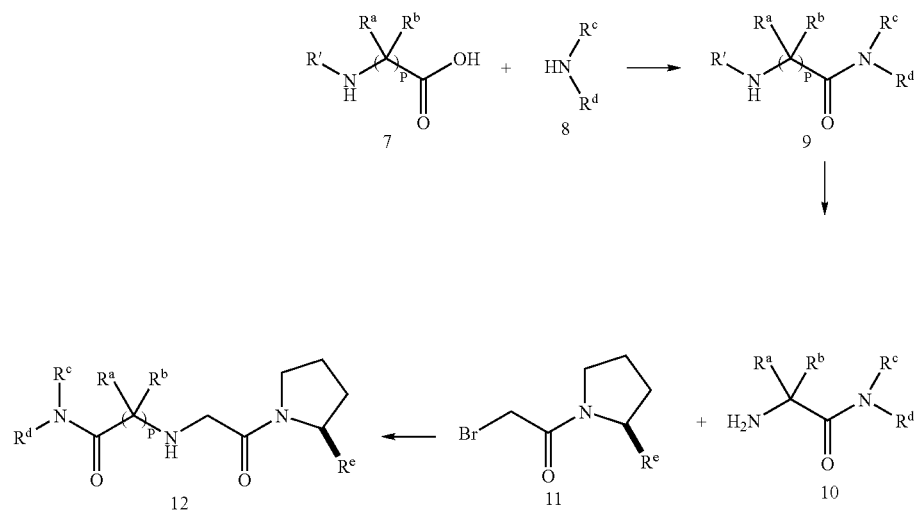

Scheme 2 illustrates another synthetic route for synthesizing pyrrolidine compounds. The starting compound is α-amino acid (7), in which the amino group is protected. This compound is coupled with amine (8) to give amide compound (9). Compound (9) is deprotected and subsequently reacted with 1-(2-bromo-acetyl)pyrrolidine (11) to afford desired pyrrolidine compound (12). Note that 1-(2-bromo-acetyl) pyrrolidine (11) can be prepared by methods well known in the art. See, e.g., *J. Med. Chem.* 2003, 46: 2774.

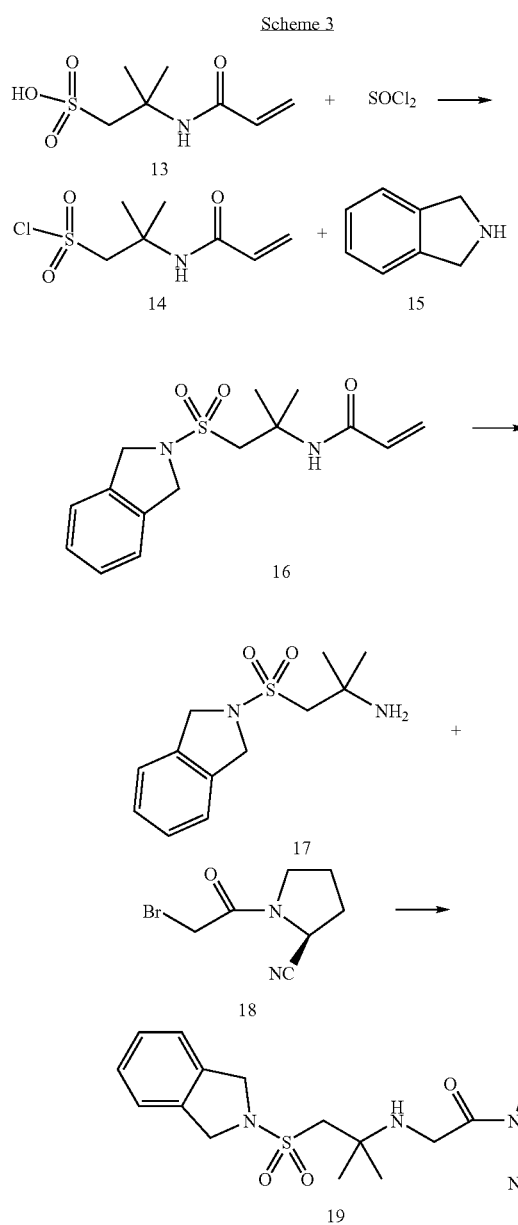

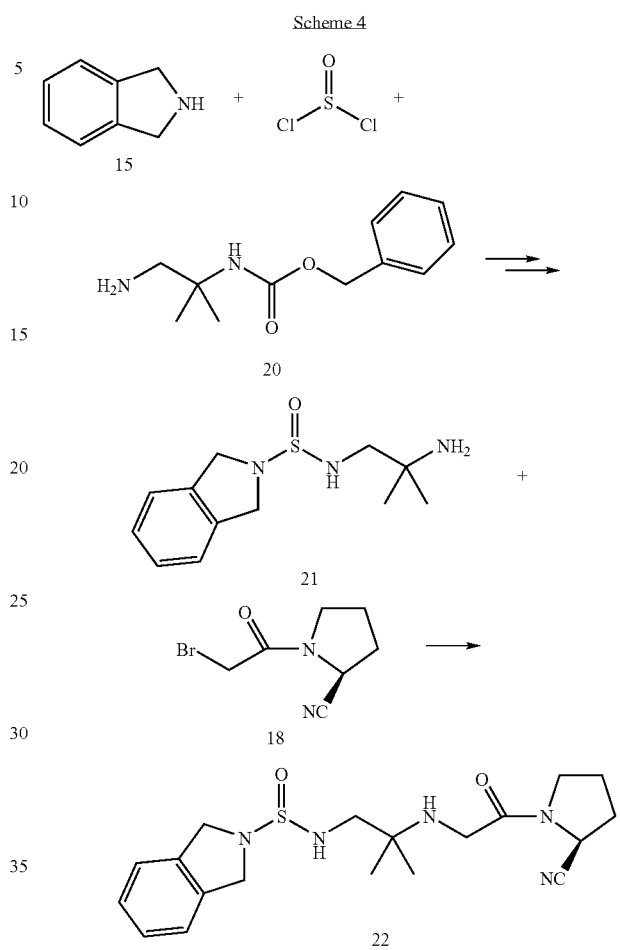

In Scheme 3, the starting compound is N-protected 2-amino-2-methyl-propane-sulfanoic acid (13), which is commercially available. It is reacted with sulfuryl chloride and then with 2,3-dihydroisoindole to give sulfonyl amide (16), which is subsequently deprotected to afford amino compound (17). This amino compound is coupled with β-bromo amide (18) to form desired pyrrolidine compound (19).

In Scheme 4, thionyl chloride is reacted with 2,3-dihydroisoindole (15) and (2-amino-1,1-dimethyl-ethyl)-carbamic acid benzyl ester (20), sequentially. The product (not shown), a protected amino compound, is deprotected to afford free amino compound (21), which is subsequently coupled with β-bromo amide (18) to form desired pyrrolidine compound (22).

Similarly, two additional pyrrolidine compounds of this invention, i.e., compounds (26) and (29), can be prepared following analoguous procedures as shown in Schemes 5 and 6 below. Starting material (24) is reportedly synthesized before. See, e.g., Boehringer M. et al., WO 2003037327.

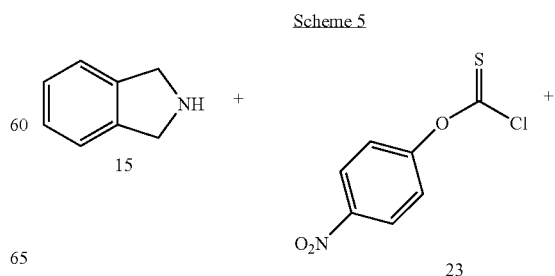

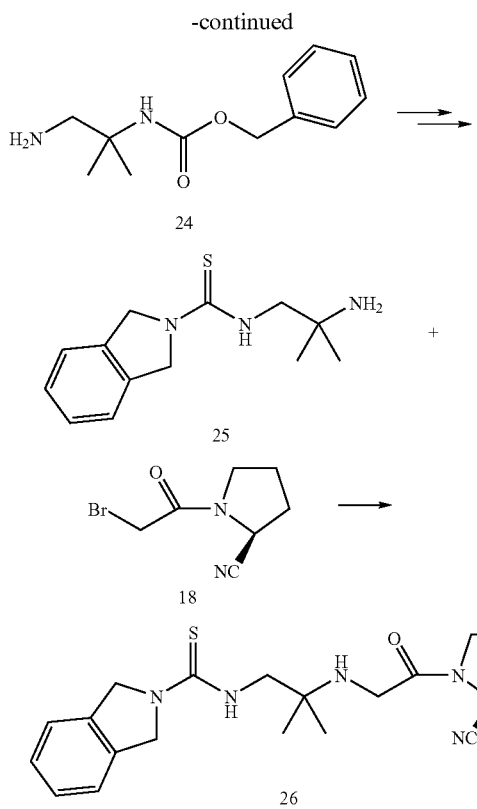

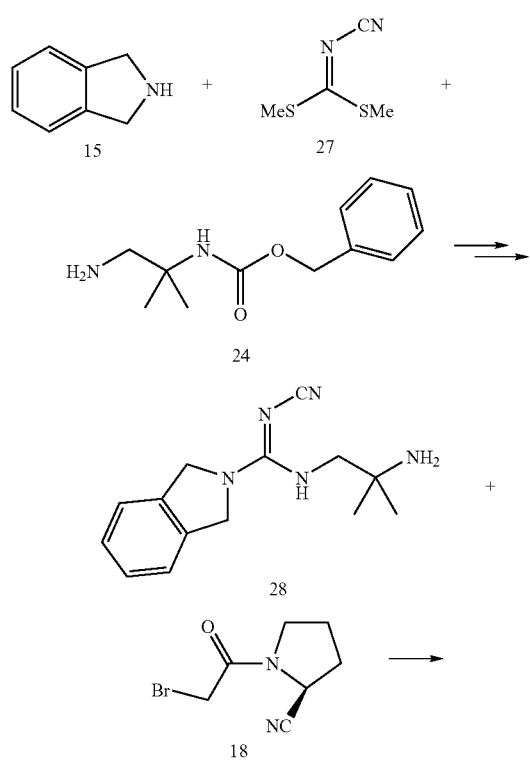

Synthetic chemistry transformations and protecting group methodologies (protection and deprotection) useful in synthesizing applicable pyrrolidine compounds are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Pyrrolidine compounds thus obtained can be further purified by column chromatography, high performance liquid chromatography, or crystallization.

This invention covers a method for inhibiting DPP-IV or DPP-VIII by contacting it with an effective amount of one or more of the pyrrolidine compounds described above. This invention also covers a method for treating Type II diabetes by administering to a subject in need thereof an effective amount of one or more of the pyrrolidine compounds described above. The term "treating" refers to application or administration of the pyrrolidine compound to a subject, who has Type II diabetes, a symptom of Type II diabetes, or a predisposition toward Type II diabetes, with the purpose to cure, heal, alleviate, relieve, alter, remedy, ameliorate, improve, or affect the disease, the symptom, or the predisposition. "An effective amount" refers to the amount of the pyrrolidine compound which is required to confer the desired effect on the subject. Effective amounts vary, as recognized by those skilled in the art, depending on route of administration, excipient usage, and the possibility of co-usage with other therapeutic treatments such as use of other active agents.

To practice the treatment method of the present invention, a composition having one or more of the pyrrolidine compounds describe above can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol and water. In addition, fixed oils are conventionally employed as a solvent or suspending medium (e.g., synthetic mono- or diglycerides). Fatty acids, such as oleic acid and its glyceride derivatives, are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having an active pyrrolidine compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active pyrrolidine compound. Examples of other carriers include colloidal silicon oxide, magnesium stearate, cellulose, sodium lauryl sulfate, and D&C Yellow # 10.

The pyrrolidine compounds of this invention can be preliminarily screened by an in vitro assay for one or more of their desired activities, e.g., inhibiting DPP-IV. Compounds that demonstrate high activities in the preliminary screening can further be screened for their efficacy by in vivo assays. For example, a test compound can administered to an animal (e.g., a mouse model) having type II diabetes and its therapeutic effects are then accessed. Based on the results, an appropriate dosage range and administration route can also be determined.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All of the publications, including patents, cited herein are hereby incorporated by reference in their entirety.

Example 1

1-[2-Amino-4-(3,4-dihydro-1H-isoquinolin-2-yl)-4-oxo-butyryl]-2-cyano-(S)-pyrrolidine, trifluoroacetic acid (TFA salt of Compound 1) was synthesized following the scheme shown below:

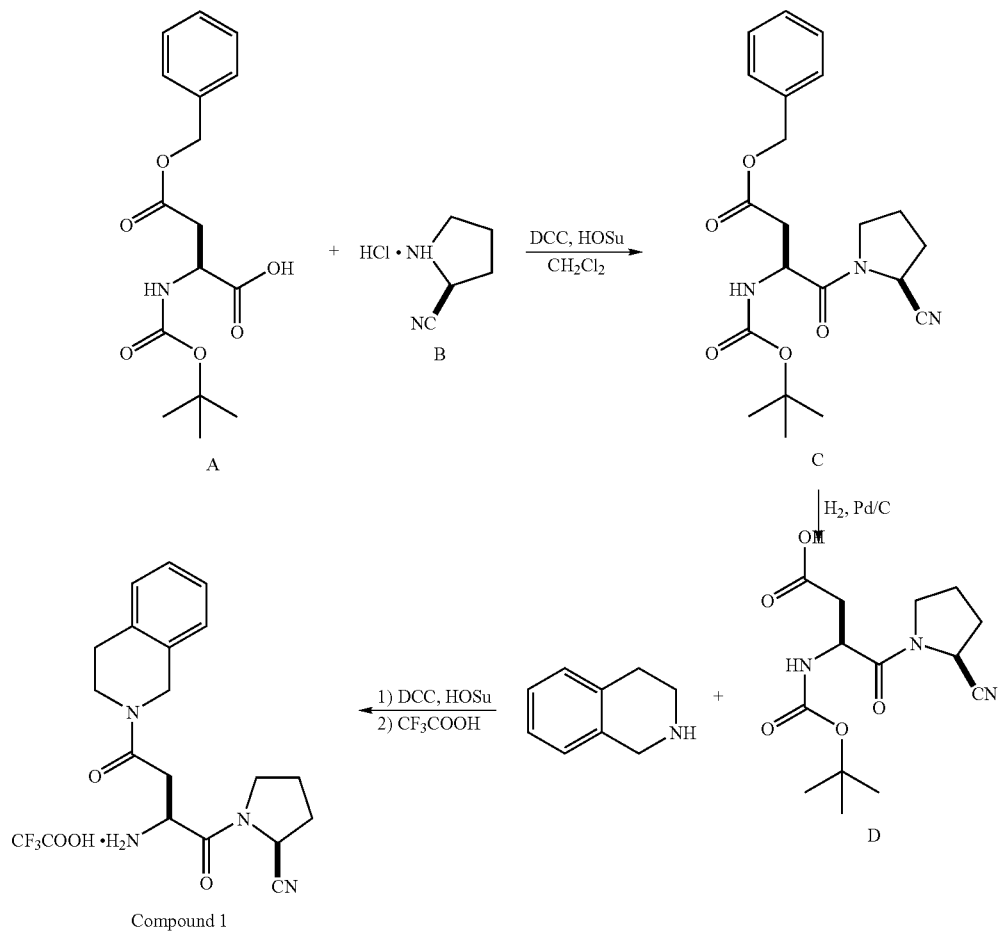

(1) Preparation of 3-t-butoxycarbonylamino-4-(2-cyano-pyrrolidin-1-yl)-4-oxo-butyric acid benzyl ester (C)

t-Butoxycarbonyl-L-glutamic acid 5-benzyl ester (A) (0.65 g, 2 mmol) and N-hydroxysuccinimide (HOSu, 0.23 g, 2 mmol) were dissolved in 6 ml of $CH_2Cl_2$/4-dioxane (2/1). The solution was cooled in an ice-water bath and dicyclohexylcarbodimide (DCC, 0.45 g, 2.2 mmol) was added with stirring. The reaction mixture was stirred at room temperature for 1 hour and then pyrrolidine-2-carbonitrile hydrochloride (B) (0.27 g, 2 mmol) and triethylamine ($Et_3N$, 0.22 g, 2.2 mmol) were added. After 4 hours at room temperature, DCC was removed by filtration and washed by $CH_2Cl_2$. The filtrate and washings were combined and washed with 10% aqueous citric acid and then saturated aqueous $NaHCO_3$, dried over $MgSO_4$, and concentrated in vacuo. Further purification by flash column chromatography (eluted with 5/4/1 hexane/$CH_2Cl_2$/EA) afforded compound (C) (80%) as a foam.

(2) Preparation of N-t-butoxycarbonyl-1-[2-amino-4-(3,4-dihydro-1H-isoquinolin-2-yl)-4-oxo-butyryl]-pyrrolidine-2-carbonitrile Compound (C) (0.40 g, 1 mmol) and 5% Pd/C (20 mg) in ethyl acetate (6 mL) and methanol (250 µL) were stirred under $H_2$ atmosphere for 7 hours. The reaction mixture was filtered and then concentrated in vacuo to give compound (D) as a white solid, which was used without further purification. A solution of compound (D) and HOSu (0.12 g, 1 mmol) in 3 ml of $CH_2Cl_2$/1,4-dioxane (2/1) was cooled in an ice-water bath. To this solution, DCC (0.23 g, 1.1 mmol) was added with stirring. After 1 hour, 1,2,3,4-tetrahydro-isoquinoline (0.20 g, 1.5 mmol) was added. The reaction mixture was stirred for 4 hours at room temperature. Then, DCC was removed by filtration and washed by $CH_2Cl_2$. The filtrate and washings were combined, washed with 10% aqueous citric acid and then saturated aqueous $NaHCO_3$, dried over $MgSO_4$, and concentrated in vacuo. Further purification by flash column chromatography (eluted with 3/6/1 hexane/$CH_2Cl_2$/EA) afforded N-t-butoxycarbonyl-1-[2-amino-4-(3,4-dihydro-1H-isoquinolin-2-yl)-4-oxo-butyryl]-pyrrolidine-2-carbonitrile (85%) as a foam.

(3) Preparation of 1-[2-amino-4-(3,4-dihydro-1H-isoquinolin-2-yl)-4-oxo-butyryl]-pyrrolidine-2-carbonitrile, trifluoroacetic acid N-t-butoxycarbonyl-1-[2-amino-4-(3,4-dihydro-1H-isoquinolin-2-yl)-4-oxo-butyryl]-pyrrolidine-2-carbonitrile (0.43 g, 1 mmol) was dissolved in cool TFA (2 mL). The resulting solution was stirred at room temperature for 10 minutes and then concentrated to provide Compound 1 as a pale yellow taffy.

MS ($ES^+$) m/z: 327.1 $(M+H)^+$, 349.1 $(M+Na)^+$.

Examples 2-18

Each of compounds 2-18 was prepared in a similar manner as described in Example 1.

6-{4-[3-Amino-4-(2-cyano-(S)-pyrrolidin-1-yl)-4-oxobutyryl]-piperazin-1-yl}-nicotinonitrile, trifluoroacetic acid (TFA salt of Compound 2)

MS ($ES^+$) m/z: 382.1 $(M+H)^+$, 404.1 $(M+Na)^+$.

1-[2-Amino-4-(6,7-dimethoxy-3,4-dihydro-1H-isoquinolin-2-yl)-4-oxobutyryl]-2-cyano-(S)-pyrrolidine, trifluoroacetic acid (TFA salt of Compound 3)

MS ($ES^+$) m/z: 387.1 $(M+H)^+$, 409.1 $(M+Na)^+$.

1-[2-Amino-4-(4-benzoylpiperazin-1-yl)-4-oxo-butyryl]-2-cyano-(S)-pyrrolidine, trifluoroacetic acid (TFA salt of Compound 4)

MS ($ES^+$) m/z: 384.1 $(M+H)^+$, 406.1 $(M+Na)^+$.

1-{2-Amino-4-[1-(2-hydroxyethyl)-6,7-dimethoxy-3,4-dihydro-1H-isoquinolin-2-yl]-4-oxobutyryl}-2-cyano-(S)-pyrrolidine, trifluoroacetic acid (TFA salt of Compound 5)

MS ($ES^+$) m/z: 453.5 $(M+Na)^+$, 469.4 $(M+K)^+$.

1-[2-Amino-4-(1-isopropyl-6,7-dimethoxy-3,4-dihydro-1H-isoquinolin-2-yl)-4-oxobutyryl]-2-cyano-(S)-pyrrolidine, trifluoroacetic acid (TFA salt of Compound 7).

MS ($ES^+$) m/z: 429.5 $(M+H)^+$, 451.5 $(M+Na)^+$.

1-[2-Amino-4-(1-benzyl-6,7-dimethoxy-3,4-dihydro-1H-isoquinolin-2-yl)-4-oxobutyryl]-2-cyano-(S)-pyrrolidine, trifluoroacetic acid (TFA salt of Compound 8)

MS ($ES^+$) m/z: 477.5 $(M+H)^+$, 499.5 $(M+Na)^+$.

1-[2-Amino-4-(1-tert-butyl-6,7-dimethoxy-3,4-dihydro-1H-isoquinolin-2-yl)-4-oxobutyryl]-2-cyano-(S)-pyrrolidine, trifluoroacetic acid (TFA salt of Compound 9)

MS ($ES^+$) m/z: 443.2 $(M+H)^+$, 465.2 $(M+Na)^+$.

3-Amino-4-(2-cyano-(S)-pyrrolidin-1-yl)-N-[2-(3,4-dimethoxy-phenyl)-ethyl]-4-oxobutyramide, trifluoroacetic acid (TFA salt of Compound 10)

$^1$H NMR ($CD_3OD$) δ: 2.09-2.31 (m, 4H), 2.69-2.88 (m, 4H), 3.29-3.43 (m, 2H), 3.60-3.73 (m, 2H), 3.78 (s, 3H, $OCH_3$), 3.81 (s, 3H, $OCH_3$), 4.47-4.52 (dd, J=7.7, 4.5 Hz, 1H), 4.78-4.82 (dd, J=7.8, 5.4 Hz, 1H, CHCN), 6.73-6.86 (m, 3H); MS ($ES^+$) m/z: 375.4 $(M+H)^+$, 397.4 $(M+Na)^+$.

3-Amino-N-benzyl-4-(2-cyano-(S)-pyrrolidin-1-yl)-4-oxobutyramide, trifluoroacetic acid (TFA salt of Compound 12)

MS ($ES^+$) m/z: 301.4 $(M+H)^+$, 323.4 $(M+Na)^+$.

3-Amino-4-(2-cyano-(S)-pyrrolidin-1-yl)-4-oxo-N-(1-phenylpropyl)butyramide, trifluoroacetic acid (TFA salt of Compound 13)

MS ($ES^+$) m/z: 329.2 $(M+H)^+$, 351.2 $(M+Na)^+$.

3-Amino-4-(2-cyano-(S)-pyrrolidin-1-yl)-N-(1-methyl-1-phenyl-ethyl)-4-oxobutyramide, trifluoroacetic acid (TFA salt of Compound 14)

$^1$H NMR ($CD_3OD$) (3 to 1 mixture of trans/cis amide rotomers) δ: 1.60~1.75 (m, 3H, $CH_3$), 2.05~2.38 (m, 4H), 2.40~2.65 (m, 2H), 3.40 (m, ¼H), 3.46~3.65 (m, 1H), 3.65~3.78 (m, ¾H), 3.96~4.05 (m, 1H), 3.65~3.78 (m, ¾H), 5.05 (d, J=7.5, 1.8 Hz, ¼H), 7.08~7.40 (m, 5H, ArH); MS ($ES^+$) m/z: 329.2 $(M+H)^+$, 351.2 $(M+Na)^+$.

3-Amino-4-(2-cyano-pyrrolidin-1-yl)-N-(2-methyl-1-phenylpropyl)-4-oxobutyramide, trifluoroacetic acid (TFA salt of Compound 16)

MS ($ES^+$) m/z: 343.2 $(M+H)^+$, 365.1 $(M+Na)^+$.

3-Amino-4-(2-cyano-(S)-pyrrolidin-1-yl)-N-(1-methoxymethyl-2-phenylethyl)-4-oxobutyramide, trifluoroacetic acid (TFA salt of Compound 17)

$^1$H NMR ($CD_3OD$) δ: 2.09-2.31 (m, 4H,), 2.62-2.90 (m, 4H,), 3.25-3.39 (m, 5H, overlapped with single at 3.32, $OCH_3$ and others), 3.56-3.69 (m, 2H), 4.18-4.23 (m, 2H), 4.34-4.48 (dd, J=7.8, 5.4 Hz, 1H), 4.78-4.82 (dd, J=7.8, 4.5 Hz, 1H, CHCN), 7.15-7.29 (m, 5H, ArH); MS ($ES^+$) m/z: 349.1 $(M+H)^+$, 381.1 $(M+Na)^+$.

3-Amino-4-(2-cyano-(S)-pyrrolidin-1-yl)-N-(2,2-dimethyl-1-phenylpropyl)-4-oxobutyramide, trifluoroacetic acid (TFA salt of Compound 18)

MS ($ES^+$) m/z: 357.2 $(M+H)^+$, 379.2 $(M+Na)^+$.

Comparative Example

2-[3-[2-[2-Cyano-(S)-pyrrolidin-1-yl]-2-oxoethylamino]-1-oxopropyl]-1,2,3,4-tetrahydroisoquinoline (comparative compound) was synthesized following the scheme shown below:

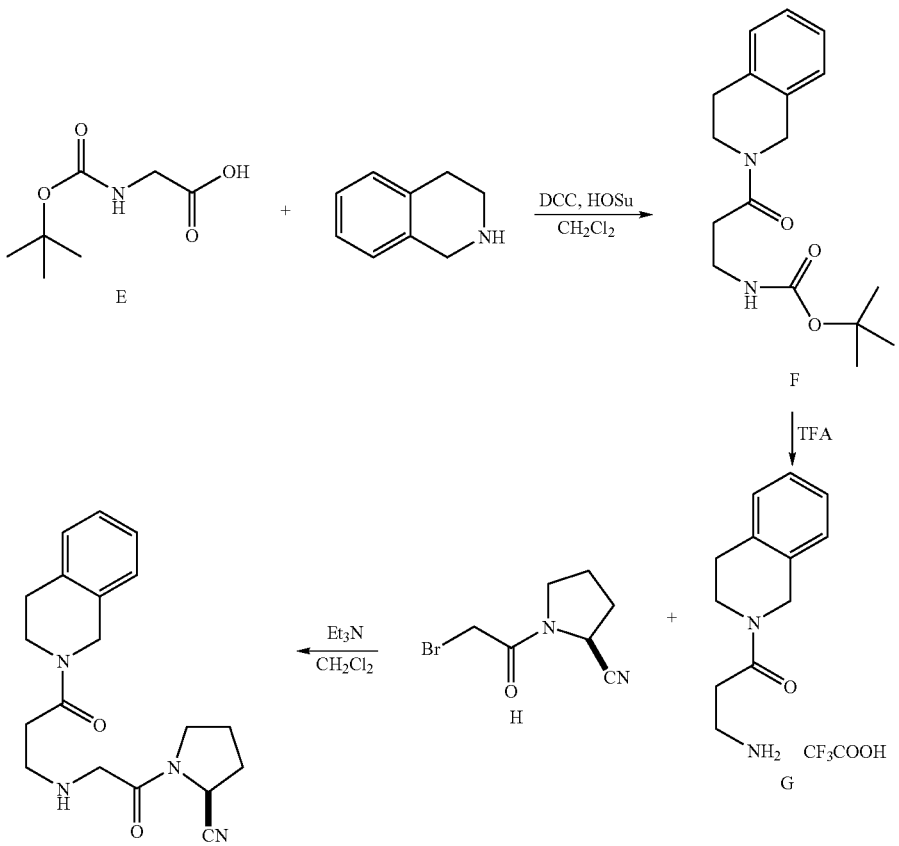

Comparative compound (1) Preparation of [3-(3,4-dihydro-1H-isoquinolin-2-yl)-3-oxo-propyl]-carbamic acid tert-butyl ester (G)

A solution of t-butoxycarbonyl-β-alanine (E) (1.89 g, 10 mmol) and HOSu (1.15 g, 10 mmol) was dissolved in 20 mL $CH_2Cl_2$/1,4-dioxane (2/1) and placed in an ice-water bath. To this solution was added DCC (2.3 g, 11 mmol) with stirring. The reaction mixture was stirred at room temperature for 1 hour and 1,2,3,4-tetrahydro-isoquinoline (2.0 g, 15 mmol) was then added. After 4 hours at room temperature, DCC was removed by filtration and washed by $CH_2Cl_2$. The filtrate and washings were combined and washed with 10% aqueous citric acid and then saturated aqueous $NaHCO_3$, dried over $MgSO_4$, and concentrated in vacuo. Further purification by flash column chromatography (eluted with $CH_2Cl_2$/EA=9/1) afforded desired compound (F) (88%) as a foam.

(2) Preparation of the Title Compound

A solution of compound (F) (0.30 g, 1 mmol) in cool TFA (2 mL) was stirred at room temperature for 10 minutes and concentrated in vacuo for 3 hours. The resultant yellow oil (G) was dissolved in $CH_2Cl_2$ and cooled in an ice-water bath. To this solution was added $Et_3N$ (0.3 g, 3 mmol) and a solution of bromide compound (H) (0.11 g, 0.5 mmol) in $CH_2Cl_2$. The reaction mixture was stirred at room temperature overnight. The mixture was diluted with $CH_2Cl_2$, and then washed with saturated aqueous $NaHCO_3$, dried over $MgSO_4$, and concentrated in vacuo. Purification by flash column chromatography (eluted with $CH_2Cl_2$/MeOH=96/4) afforded the desired compound (45%) as a light yellow oil.

$^1$H NMR ($CD_3OD$) δ: 2.16-2.28 (m, 4H), 2.87 (t, 1H, J=6.0 Hz), 2.94-2.98 (m, 3H), 3.41 (t, 2H, J=5.9 Hz), 3.46-3.51 (m, 2H), 3.63-3.68 (m, 1H), 3.73 (t, 1H, J=6.0 Hz), 3.81 (t, 1H, J=6.0 Hz), 4.11-4.13 (m, 2H), 4.70 (d, 2H, J=9.9 Hz, $ArCH_2N$), 4.81 (dd, 1H, J=9.9 and 5.1 Hz, CHCN), 7.18-7.19 (m, 4H); HRMS (EI) m/z calcd. for $C_{19}H_{24}N_4O_2$: 340.1899, found: 340.1899.

Examples 19-44

Each of Compounds 19-44 was prepared in a similar manner as described in the above example.

1-[3-[2-[2-Cyano-(S)-pyrrolidin-1-yl]-2-oxo-ethylamino]-1-oxopropyl]-4-[bis-(4-fluorophenyl)methyl]piperazine (Compound 19)

NMR ($CDCl_3$) δ: 2.62~2.18 (m, 10H), 2.91 (m, 2H), 3.20~3.80 (m, 8H), 4.22 (s, 1H), 4.75 (br d, J=6.0 Hz, ¾H), 4.82 (br d, J=6.3 Hz, ¼H), 6.95 (d, J=8.4 Hz, 2H), 6.98 (d, J=8.4 Hz, 2H), 7.31 (d, J=8.4 Hz, 2H), 7.34 (d, J=8.4 Hz, 2H); MS ($ES^+$) m/z. 496.3 $(M+H)^+$.

1-[3-[2-Cyano-(S)-pyrrolidin-1-yl]-2-oxo-ethylamino]-1-oxopropyl]-4-[2-methoxyphenyl]piperazine (Compound 20)

MS ($ES^+$) m/z: 400.2 $(M+H)^+$, 422.2 $(M+Na)^+$.

2-[3-[2-[2-Cyano-(S)-pyrrolidin-1-yl]-2-oxoethylamino]-1-oxopropyl]-1-(2-hydroxyethyl)-6,7-dimethoxy-1,2,3,4-dihydroisoquinoline (Compound 21)

MS ($ES^+$) m/z: 445.2 $(M+H)^+$, 467.3 $(M+Na)^+$.

1-[3-[2-[2-Cyano-(S)-pyrrolidin-1-yl]-2-oxoethylamino]-1-oxo-propyl]-4-[3-chlorophenyl]piperazine (Compound 22)

$^1$H NMR (CDCl$_3$) (4 to 1 mixture of trans/cis amide rotomers) δ: 2.05-2.33 (m, 4H), 2.61 (t, 2H, J=6.6 Hz), 2.92-3.03 (m, 2H), 3.14-3.21 (m, 4H), 3.38-3.46 (m, 3H, overlapped singlet at 3.46), 3.55-3.65 (m, 3H), 3.77 (t, 2H, J=5.4 Hz), 3.74-3.78 (m, ⅘H, CHCN), 4.83 (dd, ⅕H, J=7.5 and 1.8 Hz, CHCN), 6.77-6.89 (m, 3H), 7.19 (t, 1H, J=7.8 Hz); MS (ESI) m/z 404.2 (M+H)$^+$.

1-[3-[2-[2-Cyano-(S)-pyrrolidin-1-yl]-2-oxo-ethylamino]-1-oxopropyl]-4-benzoylpiperazine (Compound 23)

MS (ES$^+$) m/z: 398.3 (M+H)$^+$, 420.2 (M+Na)$^+$.

1-[3-[2-[2-Cyano-(S)-pyrrolidin-1-yl]-2-oxo-ethylamino]-1-oxopropyl]-4-[3,5-difluorobenzoyl]piperazine (Compound 24)

$^1$H NMR (CDCl$_3$) δ: 2.10-2.20 (m, 2H), 2.21-2.30 (m, 2H), 2.60 (bs, 2H), 2.85-2.95 (bm, 2H), 3.36-3.55 (m, 3H), 3.56-3.88 (m, 9H), 4.77-4.80 (m, 1H, CHCN), 6.88-6.96 (m, 3H); HRMS (EI) m/z calcd. for C$_{21}$H$_{25}$F$_2$N$_5$O$_3$: 433.1925, found: 433.1922.

1-[3-[2-[2-Cyano-(S)-pyrrolidin-1-yl]-2-oxo-ethylamino]-1-oxopropyl]-4-[4-[1-oxoethylamino]phenylsulfonyl]piperazine (Compound 25)

$^1$H NMR (CD$_3$OD) δ 2.11-2.23 (m, 7H, overlapped singlet —NHC(O)CH$_3$ at 2.13), 2.57 (t, 2H, J=6.6 Hz), 2.88 (t, 2H, J=6.6 Hz), 2.96 (bt, 2H, J=4.8 Hz), 3.01 (by, 2H, J=4.8 Hz), 3.41-3.67 (m, 8H, overlapped doublet at 3.49, J=6.0 Hz), 4.71 (t, 1H, J=5.4 Hz), 7.69-7.73 (m, 2H), 7.79-7.83 (m, 2H); MS (ES$^+$) m/z: 491.4 (M+H)$^+$, 513.3 (M+Na)$^+$.

1-[3-[2-[2-Cyano-(S)-pyrrolidin-1-yl]-2-oxo-ethylamino]-1-oxopropyl]-4-[5-cyano-2-pyridinyl]piperazine (Compound 26)

MS (ES$^+$) m/z: 396.3 (M+H)$^+$.

3-[2-(2-Cyano-(S)-pyrrolidin-1-yl)-2-oxo-ethylamino]-N-indan-2-yl-propionamide (Compound 27)

$^1$H NMR (CDCl$_3$) δ 2.50~1.80 (m, 6H), 3.00~2.60 (m, 4H), 3.70~3.10 (m, 6H), 4.63 (br s, 2H), 7.25~6.88 (m, 5H), 7.58 (br s, 1H); MS (ES$^+$) m/z: 341.1 (M+H)$^+$.

1-[3-[2-[2-Cyano-(S)-pyrrolidin-1-yl]-2-oxo-ethylamino]-1-oxopropyl]-4-(3,5-dimethoxy-benzoyl)piperazine (Compound 28)

MS (ES$^+$) m/z: 458.3 (M+H)$^+$, 480.1 (M+Na)$^+$.

N-Benzyl-3-[2-(2-cyano-(S)-pyrrolidin-1-yl)-2-oxo-ethylamino]-propionamide (Compound 30)

1H NMR (CDCl3) (4 to 1 mixture of trans/cis amide rotomers) δ: 2.05-2.32 (m, 4H), 2.45 (t, 2H, J=6.0 Hz), 2.95 (t, 2H, J=6.0 Hz), 3.31-3.57 (m, 4H, overlapped doublet at 3.38, J=3.3 Hz), 4.45 (d, 2H, J=5.7 Hz), 4.64 (dd, ⅕H, J=7.5 and 1.5 Hz, CHCN), 4.70-4.73 (m, ⅘H, CHCN), 7.22-7.36 (m, 5H), 7.56 (br s, ⅕H, ArCH2NH), 7.74 (bs, ⅘H, ArCH2NH); HRMS (EI) m/z calcd for C17H22N4O2 314.1743, found 314.1741.

N-Benzyl-3-[2-(2-cyano-(S)-pyrrolidin-1-yl)-2-oxo-ethylamino]-N-methylpropionamide (Compound 31)

MS (ES$^+$) m/z: 329.1 (M+H)$^+$.

1-[3-[2-[2-Cyano-(S)-pyrrolidin-1-yl]-2-oxo-ethylamino]-1-oxopropyl]-4-benzothiazol-2-yl]piperazine (Compound 32)

$^1$H NMR (CDCl$_3$) δ: 2.09-2.36 (m, 4H), 2.62 (t, 2H, J=6.3 Hz), 2.97-3.04 (m, 2H), 3.37-3.52 (m, 3H, overlapped singlet at 3.47), 3.53-3.81 (m, 9H), 4.74-4.78 (m, 1H), 7.09-7.14 (m, 1H), 7.29-7.35 (m, 1H), 7.56-7.64 (m, 2H); HRMS (EI) m/z calcd. for C$_{21}$H$_{26}$O$_2$S: 426.1838, found: 426.1841.

3-[2-(2-Cyano-(S)-pyrrolidin-1-yl)-2-oxo-ethylamino]-N-[2-(4-nitrophenyl)ethyl]propionamide (Compound 33)

$^1$H NMR (CDCl$_3$) δ: 2.55~1.85 (m, 6H), 2.83 (m, 2H), 2.97 (m, 2H), 3.75~3.10 (m, 6H), 4.65 (d, J=7.6 Hz, ¼H), 4.72 (m, ¾ H), 7.39 (d, J=8.4 Hz, 2H), 7.86 (m, 1H), 8.12 (d, J=8.1 Hz, 2H); MS (ES$^+$) m/z: 374.2 (M+H)$^+$.

3-[2-(2-Cyano-(S)-pyrrolidin-1-yl)-2-oxo-ethylamino]-N-(4-nitrobenzyl)propionamide (Compound 34)

$^1$H NMR (CDCl$_3$) (4 to 1 mixture of trans/cis amide rotomers) δ: 2.05-2.35 (m, 4H), 2.50 (t, 2H, J=6.0 Hz), 3.00 (t, 2H, J=6.0 Hz), 3.30-3.70 (m, 4H, overlapped doublet at 3.44, J=7.5 Hz), 4.44-4.60 (m, 2H+⅕H, overlapped doublet at 4.54, J=7.5 Hz, 2H ArCH$_2$N and ⅕H CHCN), 4.68-4.76 (m, ⅘H, CHCN), 7.50 (d, 2H, J=12.0 Hz), 8.16 (d, 2H, J=12.0 Hz), 8.28 (bt, ⅕H, ArCH$_2$NH), 8.40 (bt, ⅘H, ArCH$_2$NH); HRMS (EI) m/z calcd. for C$_{17}$H$_{21}$N$_5$O$_4$: 359.1594, found: 359.1594.

3-[2-(2-Cyano-(S)-pyrrolidin-1-yl)-2-oxo-ethylamino]-N-phenethylpropionamide (Compound 35)

$^1$H NMR (CDCl$_3$) (4 to 1 mixture of trans/cis amide rotomers) δ: 2.05-2.35 (m, 6H, overlapped triplet at 2.31, J=6.0 Hz), 2.75-2.83 (m, 4H), 3.17-3.35 (m, 3H, overlapped doublet at 3.23, J=3.0 Hz), 3.42-3.51 (m, 3H), 4.60 (dd, ⅕H, J=7.5 and 1.8 Hz, CHCN), 4.69-4.73 (m, ⅘H, CHCN), 7.16-7.27 (m, 5H), 7.29 (bs, ⅕H, ArCH$_2$CH$_2$NH), 7.5 (bs, ⅘H, ArCH$_2$CH$_2$NH); HRMS (EI) m/z calcd. for C$_{18}$H$_{24}$N$_4$O$_2$: 328.1899, found: 328.1904.

2-[3-[2-[2-cyano-(S)-pyrrolidin-1-yl]-2-oxoethylamino]-1-oxo-propyl]-1-isopropyl-1,2,3,4-dihydroisoquinoline (Compound 36)

MS (ES$^+$) m/z. 383.3 (M+H)$^+$, 405.2 (M+Na)$^+$.

3-[2-(2-Cyano-(S)-pyrrolidin-1-yl)-2-oxo-ethylamino]-N-(1-phenylpropyl)propionamide (Compound 37)

$^1$H NMR (CDCl$_3$) (9 to 1 mixture of trans/cis amide rotomers) δ: 0.88 (t, 3H, J=7.5 Hz), 1.74-1.90 (m, 2H), 2.02-2.31 (bm, 4H), 2.37-2.49 (m, 2H), 2.86-3.01 (m, 2H), 3.32-3.62 (m, 4H), 4.62 (d, ⅒H, J=7.5 Hz, CHCN), 4.73-4.77 (m, ⁹⁄₁₀H, CHCN), 4.89 (q, 1H, J=7.5 Hz), 7.22-7.40 (m, 5H), 7.81 (bt, 1H); HRMS (EI) m/z calcd. for C$_{19}$H$_{26}$N$_4$O$_2$: 342.2056 found: 342.2060.

2-[3-[2-[2-cyano-(S)-pyrrolidin-1-yl]-2-oxo-ethylamino]-1-oxo-propyl]-1-isopropyl-7-fluoro-1,2,3,4-dihydroisoquinoline (Compound 38)

MS (ES$^+$) m/z: 401.2 (M+H)$^+$.

2-[3-[2-[2-cyano-(S)-pyrrolidin-1-yl]-2-oxoethylamino]-1-oxo-propyl]-3-hydroxymethyl-1,2,3,4-dihydroisoquinoline (Compound 39)

MS (ES$^+$) m/z: 371.2 (M+H)$^+$, 393.1 (M+Na)$^+$.

2-[3-[2-[2-cyano-(S)-pyrrolidin-1-yl]-2-oxoethylamino]-1-oxo-propyl]-1-tert-butyl-7-fluoro-1,2,3,4-dihydroisoquinoline (Compound 40)

MS (ES$^+$) m/z. 415.3 (M+H)$^+$, 438.3 (M+Na)$^+$.

3-[2-(2-Cyano-(S)-pyrrolidin-1-yl)-2-oxo-ethylamino]-N-(1-methyl-1-phenylethyl)propionamide (Compound 41)

$^1$H NMR (CDCl$_3$) (9 to 1 mixture of trans/cis amide rotomers) δ 1.68 (s, 6H), 2.05-2.31 (m, 4H), 2.38-2.46 (m, 2H), 2.92-2.98 (m, 2H), 3.31-3.44 (m, 1H), 3.45-3.65 (m, 3H, overlapped singlet at 3.48), 4.67 (dd, ⅒H, J=7.5 Hz and 2.1, CHCN) 4.73-4.75 (m, ⁹⁄₁₀H, CHCN), 7.17-7.45 (m, 6H); HRMS (EI) m/z calcd. for C$_{19}$H$_{26}$N$_4$O$_2$: 342.2056, found: 342.2057.

N-Benzyl-3-[2-(2-cyano-(S)-pyrrolidin-1-yl)-2-oxo-ethylamino]-3-methylbutyramide (Compound 42)

MS (ES$^+$) m/z: 343.4 (M+H)$^+$.

3-[2-(2-Cyano-(S)-pyrrolidin-1-yl)-2-oxo-ethylamino]-3-methyl-N-phenylbutyramide (Compound 43)

MS (ES$^+$) m/z: 329.4 (M+H)$^+$.

3-[2-(2-Cyano-(S)-pyrrolidin-1-yl)-2-oxo-ethylamino]-3-methyl-N-(2-pyridin-2-yl-ethyl)butyramide (Compound 44)

$^1$H NMR (CDCl$_3$) δ: 1.08 (s, 6H), 2.31-2.2.15 (m, 7H), 2.98 (t, 2H, J=6.6 Hz), 3.27 (s, 2H), 3.55-3.36 (m, 2H), 3.64 (dd, 2H, J=6.0, 6.6 Hz), 4.76-4.73 (m, 1H), 7.11 (dd, 1H, J=7.5, 7.8 Hz), 7.17 (d, 1H, J=7.8 Hz), 7.58 (dd, 1H, J=7.5, 7.8 Hz), 8.41 (s, 1H), 8.47 (d, 1H, J=7.5 Hz); MS (ES$^+$) m/z: 358.4 (M+H)$^+$, 480.4 (M+Na)$^+$.

Example 45

1-{2-[3-(3,4-Dihydro-1H-isoquinolin-2-yl)-1,1-dimethyl-3-thioxo-propylamino]-acetyl}-pyrrolidine-2-carbonitrile (Compound 45) was synthesized following the scheme shown below.

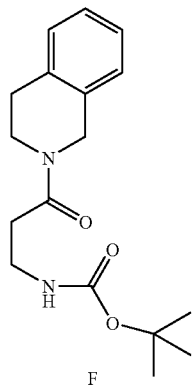

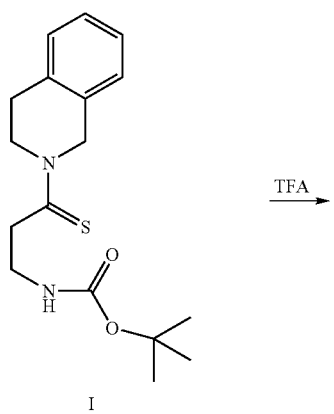

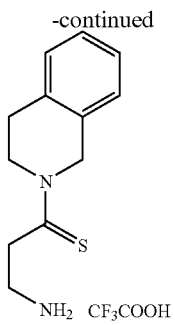

Compound (F) was transformed to thioxo compound (I) by a well-known method. See Shankaran K. et al., *Med. Chem. Lett.* 2004, 14 (17): 4539-4544. Compound (I) was then deprotected by TFA and coupled with compound (H) following the procedures described in the comparative example above to provide compound 45.

Example 46

DPP-IV was purified from human semen according to the method described in de Meester et al. (de Meester et al. (1996) J. Immun. Method 189: 99-105) with minor modifications. Briefly, the semen was diluted with 50 ml of phosphate buffered saline (PBS) and centrifuged at 900×g for 10 minutes. The supernatant was centrifuged again at 105,000×g for 120 minutes to separate prostasomes and seminal plasma. The prostasomes, i.e., pellets, and the seminal plasma, i.e., supernatant, were both used for further purification of DPP-IV. The pellets were washed twice with 20 mM Tris-HCl (pH 7.4), and then incubated in 20 mM Tris-HCl (pH 7.4), 1% Triton X-100 for 1 hour at 4° C. The resulting solution was centrifugated at 40,000×g for 10 minutes to remove prostasomes debris before dialyzed against 20 mM Tris-HCl (pH 7.4), 70 mM NaCl, and 0.1% Triton X-100. The solution was then passed through a DEAE-Sepharose fast flow column (2.6×10 cM) equilibrated with 20 mM Tris-HCl (pH 7.4), 70 mM NaCl and 0.1% Triton X-100 at a flow rate of 2 ml/min. The column was subsequently eluted with 300 ml NaCl (70 to 350 mM) with a linear gradient at a flow rate of 3 ml/min. Positive fractions were pooled and adjusted to pH 8.0 by 0.5 M Tris-HCl (pH 8.0) before applied to an adenosine deaminase-Sepharose columns. The column was prepared as described in de Meester et al. After the column was washed with 10 column volumes of equilibration buffer and then with an equal amount of 50 mM Tris-HCl (pH 7.4) containing 0.5 M NaCl and 0.1% Triton X-100, DPP-IV was eluted with 2 mM Tris-HCl (pH 8.0) containing 0.1% Triton X-100. The supernatant was denatured in 20 mM Tris-HCl (pH 7.4), 1% Tris X-100 for 1 hour at 4° C. The resulting solution was handled as described above to obtain purified DPP-IV.

DPP-VIII was also expressed and purified. Briefly, Full length Human DPP-VIII cDNA was amplified by RT-PCR from a human liver cDNA library with the primers 5'-AAGCTTCCATGGCAGCAGCAATGGAAACA-3' and 5'-GCGGCCGCTTATATCACTTTTAGAGCAGCAATA-3'. The resulting fragments were cloned into pCR®-Blunt II-Topo vector (Invitrogen). The full length DPP-VIII cDNA fragment was released by digestion with HindIII (blunt) and Not I, and then ligated into the baculovirus expression vector pBac-PAC-His2 (Clontech). The plasmid was transfected into Sf9 cells to obtain recombinant virus. Further amplifications of the virus were conducted. Briefly, virus titers were determined by end-point dilution assays. Baculovirus infections were carried out as follows: the Sf9 cells were cultured in 6-well plates to reach a concentration of $10^6$ cells per well. The culture media were removed and replaced by virus inoculum at a multiplicity of infection (M.O.I.) of 0.1 $TCID_{50}$/cell ($TCID_{50}$ is 50% tissue-culture infectious dose). After removing media containing the unbound virus, fresh media were added and the cells were incubated at 27° C. for 72 to 96 hours. The Sf9 cells were infected at an M.O.I. of 0.5 $TCID_{50}$/cell and were harvested at 72 hours post-transfection for subsequent protein purification. The purification of DPP-VIII was done by a Ni-NTA column. The Sf9 cells expressing DPP-VIII were pelleted and resuspended in binding buffer containing 50 mM sodium phosphate buffer (pH 7.6) and 300 mM NaCl. The cells were sonicated and the cleared lysates were passed through a Ni-affinity column. The column was washed by three to five bed volume of a binding buffer containing 10 mM imidazole, a binding buffer containing 30 mM imidazole, and a binding buffer containing 120 mM imidazole. Note that expression of DPP-VIII was tracked by fluorescent eGFP expression or protein activity assays using H-Gly-Pro-pNA as a substrate.

The purity of DPP-IV and DPP-VIII was checked by SDS-PAGE, followed by commassie blue stain or silver stain. Concentrations of DPP-IV and DPP-VIII were measured by the method of Bradford using BSA as the standard (Bradford, M. M. (1976) *Anal. Biochem.* 72, 248-254.)

The biological activities of DPP-IV and DPP-VIII were confirmed by measuring enzymatic kinetic constants. As an example, the kinetic constant of DPP-IV was measured as follows:

All reactions were carried out in PBS using H-Gly-Pro-pNA as a substrate in the presence of 10 nM DPP-IV. The reactions were monitored and measured at OD 405 nm. The initial rate was measured when less than 10% substrate was depleted. The steady state parameters, $k_{cat}(=V_{max}/[E])$ and $K_m$, were determined from initial velocity measurements at 0.5-5 $K_m$ of the substrate concentrations for the first 300 seconds. Lineweaver-Burk plots were obtained using non-linear regression of the classic Michaelis-Menten equation (equation 1) to obtain $K_m$ values. The $k_{cat}$ was calculated from $V_{max}/[E]$ with the molecular weight of DPP-IV taken as 85,000.

$$V_0 = V_{max}[S]/(K_m+[S]) \quad \text{(equation 1)}$$

where $V_0$ is the initial velocity, [S] is the substrate concentration, $V_{max}$ is the maximum velocity and $K_m$ is the Michaelis constant. Correlation coefficients better than 0.990 were obtained throughout.

A number of compounds of this invention and the comparative compound were tested for their $IC_{50}$ values for inhibiting DPP-IV. $IC_{50}$ determination was carried out at 37° C. in 20 mM Tris-HCl (pH 8.0) or in PBS, with purified human semen DPP-IV. The substrate used was 500 uM H-Gly-Pro-pNA. For each compound, eight to twelve serial dilutions were assayed to generate data points, from which the $IC_{50}$ value was calculated using the Sigma plot. All tested compounds exerted inhibitory activities against DPP-IV. It was unexpected that Compound 45, which has a thioxo group, inhibited DPP-IV more effectively than the comparative compound, which has an oxo group.

Similarly, $IC_{50}$ values for inhibiting DPP-VIII in PBS containing 2.5 mM H-Gly-Pro-pNA as a substrate were also obtained on a number of compounds of this invention. All tested compounds showed inhibitory activities against DPP-VIII.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous to pyrrolidine compounds of this invention also can be made, screened for their inhibitory activities against DPP-IV and treating Type II diabetes and used to practice this invention. Thus, other embodiments are also within the claims.

What is claimed is:
1. A compound of the following formula:

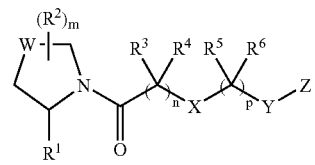

wherein
$R^1$ is H or CN;
each of $R^2$, $R^3$, $R^4$, $R^5$, and $R^6$, independently, is H, halo, nitro, cyano, amino, hydroxy, alkyl, haloalkyl, alkoxy, aryloxy, aralkyl, cyclyl, heterocyclyl, aryl, or heteroaryl;
m is 0, 1, 2, 3, 4, or 5;
each of n and p, independently, is 0, 1, 2, 3, or 4;
W is $CR^aR^{a'}$, in which $R^a$ and $R^{a'}$, independently, is H, halogen, alkyl, or aryl;
X is O, S, or $CR^b(NR^{b'}R^{b''})$, in which $R^b$, $R^{b'}$, and $R^{b''}$, independently, is H, alkyl, or aryl; Y is

and

Z is NR⁷R⁸, in which each of $R^7$ and $R^8$, independently, is H, alkyl, alkoxyalkyl, haloalkyl, cyclyl, heterocyclyl, aryl, aralkyl, heteroaryl, or heteroaralkyl; or NR⁷R⁸, together, is a 3-8 membered ring having 1 or 2 heteroatoms, optionally substituted with halo, CN, $NO_2$, —$OR^d$, alkyl, aryl, heteroaryl, haloalkyl, —$C(O)R^d$, —$SR^d$, $S(O)R^d$, —$S(O)_2R^d$, $NR^cR^{d'}$, —$C(O)OR^d$, —$C(O)NR^dR^{d'}$, —$OC(O)R^d$, —$NR^dC(O)R^{d'}$, —$NR^dC(O)OR^{d'}$, or —$NR^dC(O)NR^{d'}R^{d''}$, or optionally fused with one of cyclyl, heterocyclyl, aryl, and heteroaryl, each of $R^d$, $R^{d'}$, and $R^{d''}$, independently, being H, alkyl, or aryl.

2. The compound of claim 1, wherein W is $CH_2$, $R^1$ is CN, and m is 0.

3. The compound of claim 2, wherein X is $CHNH_2$.

4. The compound of claim 3, wherein n is 0 and p is 1.

5. The compound of claim 4, wherein is

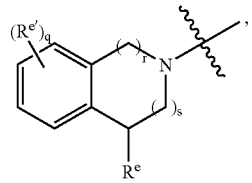

, in which $R^e$ is alkyl, haloalkyl, alkoxy, aryloxy, aralkyl, cyclyl, heterocyclyl, aryl, or heteroaryl;

$R^{e'}$ is halo, nitro, cyano, amino, hydroxy, alkyl, haloalkyl, alkoxy, aryloxy, aralkyl, cyclyl, heterocyclyl, aryl, or heteroaryl; q is 0, 1, 2, 3, or 4; and each of r and s, independently, is 0, 1, or 2.

6. The compound of claim 4, wherein Z is 5 or 6 membered ring optionally substituted with halo, CN, $NO_2$, —$OR^d$, alkyl, aryl, heteroaryl, haloalkyl, —$C(O)R^d$, —$SR^d$, —$S(O)R^d$, —$S(O)_2R^d$, —$NR^cR^{d'}$, —$C(O)OR^d$, —$C(O)NR^dR^{d'}$, —$OC(O)R^d$, —$NR^dC(O)R^{d'}$, —$NR^dC(O)OR^{d'}$, or —$NR^dC(O)NR^{d'}R^{d''}$.

7. The compound of claim 4, wherein $R^7$ is H and $R^8$ is alkyl, cyclyl, aryl, or aralkyl.

8. The compound of claim 1, wherein the compound is
1-[2-amino-4-(3,4-dihydro-1H-isoquinolin-2-yl)-4-oxo-butyryl]-2-cyano-(S)-pyrrolidine;
6-{4-[3-amino-4-(2-cyano-(S)-pyrrolidin-1-yl)-4-oxobutyryl]-piperazin-1-yl}-nicotinonitrile;
1-[2-Amino-4-(1,3-dihydro-isoindol-2-yl)-4-oxo-butyryl]-pyrrolidine-2-carbonitrile;
1-[2-amino-4-(4-benzoylpiperazin-1-yl)-4-oxo-butyryl]-2-cyano-(S)-pyrrolidine;
1-{2-amino-4-[1-(2-hydroxyethyl)-6,7-dimethoxy-3,4-dihydro-1H-isoquinolin-2-yl]-4-oxo-butyryl}-2-cyano-(S)-pyrrolidine;
1-[2-amino-4-(6,7-dimethoxy-3,4-dihydro-1H-isoquinolin-2-yl)-4-oxo-butyryl]-pyrrolidine-2-carbonitrile;
1-[2-amino-4-(1-isopropyl-6,7-dimethoxy-3,4-dihydro-1H-isoquinolin-2-yl)-4-oxo-butyryl]-2-cyano-(S)-pyrrolidine;
1-[2-amino-4-(1-benzyl-6,7-dimethoxy-3,4-dihydro-1H-isoquinolin-2-yl)-4-oxo-butyryl]-2-cyano-(S)-pyrrolidine;
1-[2-amino-4-(1-tert-butyl-6,7-dimethoxy-3,4-dihydro-1H-isoquinolin-2-yl)-4-oxo-butyryl]-2-cyano-(S)-pyrrolidine;
3-amino-4-(2-cyano-(S)-pyrrolidin-1-yl)-N-[2-(3,4-dimethoxy-phenyl)-ethyl]-4-oxo-butyramide;
1-[2-amino-4-(3-hydroxymethyl-3,4-dihydro-1H-isoquinolin-2-yl)-4-oxo-butyryl]-2-cyano-(S)-pyrrolidine;
3-amino-N-benzyl-4-(2-cyano-(S)-pyrrolidin-1-yl)-4-oxo-butyramide;
3-amino-4-(2-cyano-(S)-pyrrolidin-1-yl)-4-oxo-N-(1-phenylpropyl)butyramide;
3-amino-4-(2-cyano-(S)-pyrrolidin-1-yl)-N-(1-methyl-1-phenyl-ethyl)-4-oxo-butyramide;
1-[2-amino-4-(1,1-dimethyl-6,7-dimethoxy-3,4-dihydro-1H-isoquinolin-2-yl)-4-oxo-butyryl]-2-cyano-(S)-pyrrolidine;
3-amino-4-(2-cyano-pyrrolidin-1-yl)-N-(2-methyl-1-phenylpropyl)-4-oxobutyramide;
3-amino-4-(2-cyano-(S)-pyrrolidin-1-yl)-N-(1-methoxymethyl-2-phenylethyl)-4-oxo-butyramide; or
3-amino-4-(2-cyano-(S)-pyrrolidin-1-yl)-N-(2,2-dimethyl-1-phenylpropyl)-4-oxo-butyramide.

9. A compound of the following formula:

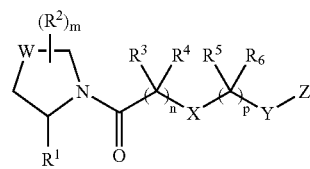

wherein
$R^1$ is H or CN;
each of $R^2$, $R^3$, $R^4$, $R^5$, and $R^6$, independently, is H or alkyl;
m is 0, 1, 2, 3, 4, or 5;
n is 0, 1, 2, 3, or 4;
p is 2 or 3;
W is $CR^aR^{a'}$, in which $R^a$ and $R^{a'}$, independently, is H, halogen, alkyl, or aryl;
Y is

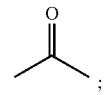

Z is NR⁷R⁸, in which each of $R^7$ and $R^8$, independently, is H; alkyl; alkoxyalkyl; haloalkyl; aralkyl; heteroaralkyl; or a 3-8 membered monocyclic ring optionally substituted with halo, CN, $NO_2$, —$OR^d$, alkyl, aryl, heteroaryl, haloalkyl, —$C(O)R^d$, —$SR^d$, —$S(O)R^d$, —$S(O)_2R^d$, —$NR^cR^{d'}$, —$C(O)OR^d$, —$C(O)NR^dR^{d'}$, —$OC(O)R^d$, —$NR^dC(O)R^{d'}$, —$NR^dC(O)OR^{d'}$, or —$R^dC(O)NR^{d'}R^{d''}$; or NR⁷R⁸, together, is a 3-8 membered monocyclic ring having 1 or 2 heteroatoms, optionally substituted with halo, CN, $NO_2$, —$OR^d$, alkyl, aryl, heteroaryl, haloalkyl, —$C(O)R^d$, —$SR^d$, —$S(O)R^d$, —$S(O)_2R^d$, —$NR^cR^{d'}$, —$C(O)OR^d$, —$C(O)NR^dR^{d'}$, —$OC(O)R^d$, —$NR^dC(O)R^{d'}$, —$NR^dC(O)OR^{d'}$, or —$NR^dC(O)NR^{d'}R^{d''}$; each of $R^d$, $R^{d'}$, and $R^{d''}$, independently, being H, alkyl, or aryl.

10. The compound of claim 9, wherein W is CH$_2$, R$^1$ is CN, and m is 0

11. The compound of claim 10, wherein X is NH.

12. The compound of claim 11, wherein n is 1 and p is 2.

13. The compound of claim 12, wherein NR$^7$R$^8$, together, is 5- or 6-membered monocylic ring.

14. The compound of claim 12, wherein R$^7$ is H or alkyl, and R$^8$ is aralkyl.

15. The compound of claim 9, wherein the compound is
1-[3-[2-[2-cyano-(S)-pyrrolidin-1-yl]-2-oxo-ethylamino]-1-oxo-propyl]-4-[bis-(4-fluorophenyl)methyl]piperazine;
1-[3-[2-cyano-(S)-pyrrolidin-1-yl]-2-oxo-ethylamino]-1-oxo-propyl]-4-12-methoxyphenyl]piperazine;
1-[3-[2-[2-cyano-(S)-pyrrolidin-1-yl]-2-oxo-ethylamino]-1-oxopropyl]-4-[3-chlorophenyl]piperazine;
1-[3-[2-[2-cyano-(S)-pyrrolidin-1-yl]-2-oxo-ethylamino]-1-oxopropyl]-4-benzoylpiperazine;
1-[3-[2-[2-cyano-(S)-pyrrolidin-1-yl]-2-oxo-ethylamino]-1-oxopropyl]-4-[3,5-difluorobenzoyl]piperazine;
1-[3-[2-[2-cyano-(S)-pyrrolidin-1-yl]-2-oxo-ethylamino]-1-oxopropyl]-4-[4-[1-oxoethylamino]phenylsulfonyl]piperazine;
1-[3-[2-[2-cyano-(S)-pyrrolidin-1-yl]-2-oxo-ethylamino]-1-oxopropyl]-4-[5-cyano-2-pyridinyl]piperazine;
1-[3-[2-[2-cyano-(S)-pyrrolidin-1-yl]-2-oxo-ethylamino]-1-oxopropyl]-4-(3,5-dimethoxy-benzoyl)piperazine;
1-{2-[3-(3-benzoyl-imidazolidin-1-yl)-3-oxo-propylamino]-acetyl}-pyrrolidine-2-carbonitrile;
N-benzyl-3-[2-(2-cyano-(S)-pyrrolidin-1-yl)-2-oxo-ethylamino]-propionamide;
N-benzyl-3-[2-(2-cyano-(S)-pyrrolidin-1-yl)-2-oxo-ethylamino]-N-methylpropionamide;
1-[3-[2-[2-cyano-(S)-pyrrolidin-1-yl]-2-oxo-ethylamino]-1-oxopropyl]-4-benzothiazol-2-yl]piperazine;
3-[2-(2-cyano-(S)-pyrrolidin-1-yl)-2-oxo-ethylamino]-N-[2-(4-nitrophenyl)ethyl]propionamide;
3-[2-(2-cyano-(S)-pyrrolidin-1-yl)-2-oxo-ethylamino]-N-(4-nitrobenzyl)propionamide;
3-[2-(2-cyano-(S)-pyrrolidin-1-yl)-2-oxo-ethylamino]-N-phenethylpropionamide;
3-[2-(2-cyano-(S)-pyrrolidin-1-yl)-2-oxo-ethylamino]-N-(1-phenylpropyl)propionamide;
3-[2-(2-cyano-(S)-pyrrolidin-1-yl)-2-oxo-ethylamino]-N-(1-methyl-1-phenylethyl)propionamide;
N-benzyl-3-[2-(2-cyano-(S)-pyrrolidin-1-yl)-2-oxo-ethylamino]-3-methylbutyramide; or
3-[2-(2-cyano-(S)-pyrrolidin-1-yl)-2-oxo-ethylamino]-3-methyl-N-(2-pyridin-2-yl-ethyl)butyramide.

16. A method of inhibiting dipeptidyl peptidase IV, comprising contacting dipeptidyl peptidase IV with an effective amount of a compound of claim 1.

17. A method of inhibiting dipeptidyl peptidase IV, comprising contacting dipeptidyl peptidase IV with an effective amount of a compound of claim 9.

18. A method of treating Type II diabetes, comprising administering to a subject in need thereof an effective amount of a compound of claim 1.

19. A method of treating Type II diabetes, comprising administering to a subject in need thereof an effective amount of a compound of claim 9.

20. The compound of claim 1, wherein each of R$^a$ and R$^{a'}$, independently, is H or F.

21. The compound of claim 9, wherein each of R$^a$ and R$^{a'}$, independently, is H or F.

* * * * *